(12) United States Patent
Cabak et al.

(10) Patent No.: US 6,460,262 B1
(45) Date of Patent: Oct. 8, 2002

(54) LOCKING CUFF SIZER AND METHOD FOR MEASURING GIRTH OF A BODY PASSAGE

(75) Inventors: James E. Cabak, Plymouth, MN (US); Carrie Ann Voda, Minneapolis, MN (US); Kyle E. Nevala, Minneapolis, MN (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 09/505,547

(22) Filed: Feb. 17, 2000

(51) Int. Cl.[7] .............................. A61B 1/00; G01B 3/10
(52) U.S. Cl. ...................... 33/512; 33/511; 33/555.4; 33/759
(58) Field of Search .................. 33/511, 512, 555.1, 33/555.4, 755, 758, 759; 600/587, 29, 30

(56) References Cited

U.S. PATENT DOCUMENTS

| | | | |
|---|---|---|---|
| 4,333,241 A | * | 6/1982 | Wasik et al. ............... 33/555.4 |
| 4,474,187 A | * | 10/1984 | Timm et al. .................. 600/29 |
| 4,685,474 A | * | 8/1987 | Kurz et al. .................... 33/512 |
| 4,974,331 A | | 12/1990 | Watterson |
| 5,445,626 A | * | 8/1995 | Gigante ........................ 600/30 |
| 5,478,305 A | | 12/1995 | Craggs |
| 5,887,593 A | * | 3/1999 | Levius ......................... 600/29 |
| 5,893,826 A | * | 4/1999 | Salama ......................... 600/31 |
| 6,068,591 A | * | 5/2000 | Bruckner et al. ............. 600/30 |
| 6,110,200 A | * | 7/2000 | Hinnenkamp ................ 33/512 |

* cited by examiner

*Primary Examiner*—Christopher W. Fulton
*Assistant Examiner*—Yaritza Guadalupe
(74) *Attorney, Agent, or Firm*—Jeffrey J. Hohenshell

(57) ABSTRACT

An apparatus and method for measuring the size of a body passage is provided. The apparatus comprises a flexible strip having first and second ends. At least one aperture is disposed on the strip between the first and second ends. An indicia of body passage circumference is disposed on the strip in association with the at least one aperture. The body passage may be measured by inserting the strip into a dissected tunnel around the body passage, manipulating the strip such that the strip substantially surrounds the body passage, and observing the indicia on the strip to generally determine the circumference of the body passage.

40 Claims, 4 Drawing Sheets

LOCKING CUFF SIZER AND METHOD FOR MEASURING GIRTH OF A BODY PASSAGE

FIELD OF THE INVENTION

The invention relates generally to cuff sizers for estimating the girth of a body passage and particularly to cuff sizers used in procedures for the implantation of artificial sphincters.

BACKGROUND OF THE INVENTION

Incontinence is the inability to voluntarily control the discharge of excretory materials and is typically caused by physical, neurological or psychological traumas. Incontinence is a major medical problem that affects millions of people and extends across all age groups. Moreover, this condition often results in serious discomfort and embarrassment of the patient, often forcing those affected to withdraw from regular social activities.

To address and treat incontinence and to assist affected patients in returning to a degree of normalcy in this area, surgical processes and devices have been developed which are intended to restore the lost anatomical functions. Many of these surgical processes employ devices whose function it is to selectively occlude the affected body passage upon the desire of the patient. Inflatable fluid actuated artificial urinary sphincters (AUS) are one type of such known devices and their function is to selectively occlude the urethra. Fluid actuated artificial bowel sphincters (ABS) are another type of device and their function is to selectively occlude the anus.

Referring to FIG. 1, an example of a fluid actuated ABS 10 is illustrated. However, it should be noted that an AUS has a similar configuration. The ABS 10 includes an inflatable cuff 12 configured to surround and occlude the anus 14, a pressure regulating balloon 16 to store actuating fluid, and a control pump 18 to transfer the actuating fluid from the balloon 16 to the cuff 12 and from the cuff 12 to the balloon 16.

For a female patient, the pump 18 is implanted in the labia 20, and the balloon 16 is implanted in the abdomen such as the space of retzius. For a male patient, the pump may be implanted in the scrotum, and the balloon may be implanted in the abdomen such as the space of retzius.

The basic components of these devices are connected by fluid transmission lines 24, 26. One fluid transmission line 24 or conduit connects the cuff 12 with the pump 18, and the second fluid transmission line 26 or conduit connects the pump 18 with the balloon 16. The cuff 12 is inflated to occlude the anus 14 and deflated to allow the discharge of feces through the anus 14. Normally, the cuff 12 is maintained in an inflated (closed) position.

One of the difficulties associated with an inflatable fluid actuated sphincter is that the implanted cuff may be improperly sized for the particular anus or urethra due to the difficultiness of determining the anal or urethral girth during surgery. A cuff which is over-sized may lead to unreliable coaptation or closure of the anal or urethral tissue, thus defeating the purpose of implanting the cuff, while a cuff which under-sized may cause damage to the circumscribed tissue or unduly restrict the size of the cuffed passage. Thus, there exists a need for a device and method to assist the surgeons in a more accurate determination of the anal or urethral girth of a patient for selecting an appropriately sized cuff during the surgical procedure.

BRIEF SUMMARY OF THE INVENTION

In accordance with the present invention, a locking cuff sizer for determing the size of a body passage is provided. The cuff sizer is particularly suited for properly sizing the anal or urethral girth during surgical implantation of an ABS or AUS device. In accordance with an illustrative embodiment of the present invention, the cuff sizer includes a flexible strip having first and second ends. A plurality of apertures are disposed between the first and second ends of the strip, and the plurality of apertures are aligned along a longitudinal axis of the strip. Indices of body passage circumference are disposed on the strip in association with each of the plurality of apertures. An adapter is disposed near the first end of the strip, and the adapter engages with one of the plurality of holes to lock the cuff sizer around the body passage.

The strip is inserted into a dissected tunnel around the body passage and manipulated such that the strip substantially surrounds the body passage. By securing the adapter onto one of the plurality of apertures, the cuff sizer is locked around the circumference of the body passage. Once "locked", the surgeon may evaluate the tightness of the "locked" position by sliding the cuff sizer along the body passage. If the cuff sizer is overly tight or loose, it may be "unlocked" and another aperture may be selected. When the appropriate aperture is selected, measurement of the body passage may be observed by viewing the indicia in association with the appropriate aperture. After determining the correct cuff size, the cuff sizer is removed, and a correctly sized cuff is implanted into the patient.

To aid in the insertion, manipulation, and securement of the cuff sizer around the circumference of the body passage, the cuff sizer may include an introducer such as a flexible tubing having first and second ends, wherein the first end is connected to the adapter. The cuff sizer may be introduced into the dissected tunnel by first inserting the introducer through the dissected tunnel. The strip may then be drawn through the dissected tunnel by pulling the introducer. The cuff sizer may then be secured into its "locked" position by passing the second end of the introducer through the desired aperture and securing the adapter onto the appropriate aperture.

Other objects, features, and advantages of the present invention will become apparent from a consideration of the following detailed description.

DETAILED DESCRIPTION OF THE PREFERRED EMBODIMENTS

Figure 1:
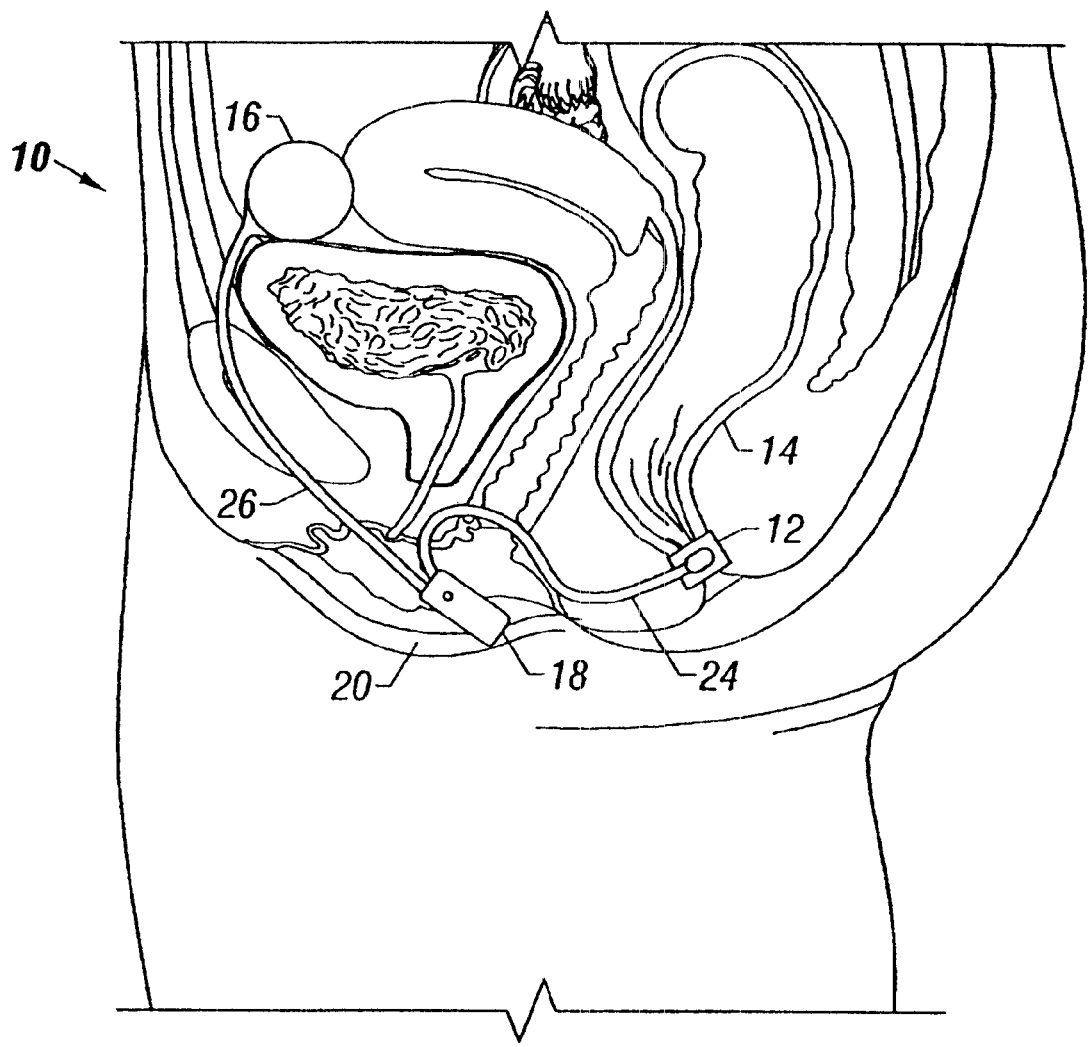
FIG. 1 is an artifical bowel sphincter as placed in a patient
Figure 2:
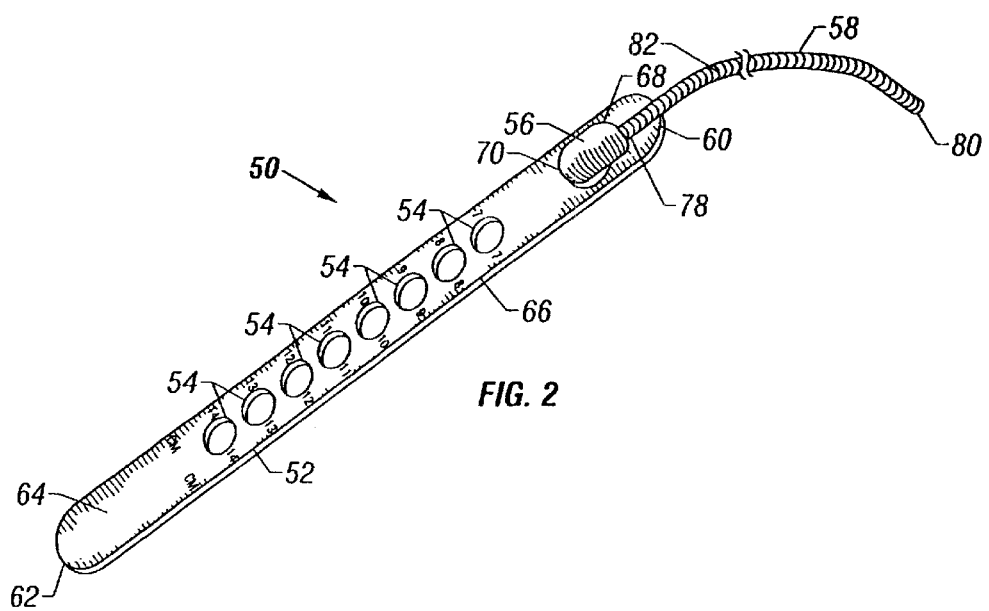
FIG. 2 is a perspective view of a locking cuff sizer in accordance with the present invention.
Figure 3:
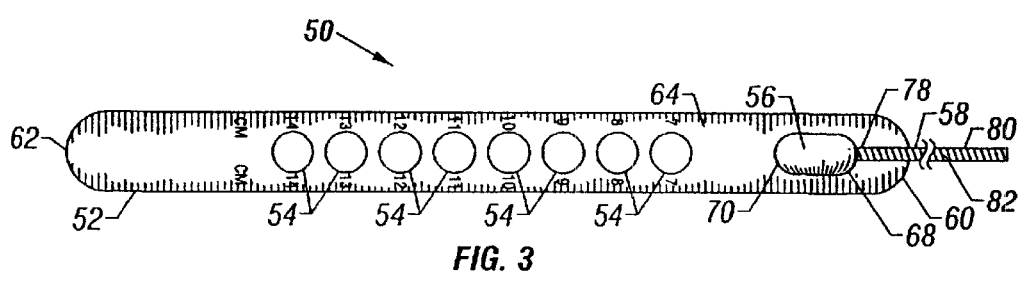
FIG. 3 is a plan top view of the locking cuff sizer shown in FIG. 2.
Figure 4:
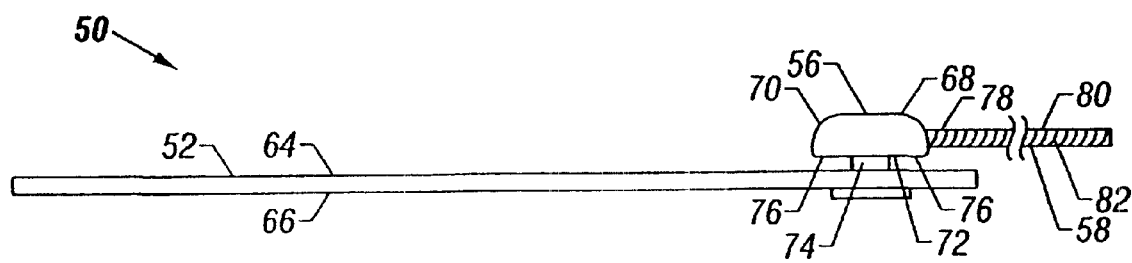
FIG. 4 is a plan side view of the locking cuff sizer shown in FIG. 2.

Referring to FIGS. 2–4, an exemplary embodiment of a locking cuff sizer 50 of the present invention is illustrated for determining anal girth and includes a tape element 52, a plurality of holes 54, an adapter 56, and an introducer 58. A similarly constructed device is usable for determining urethral girth.

The tape element 52 is approximately 23 cm in length, 2 cm in width, and 0.1 cm in thickness, however, depending on the size of the anus, smaller or larger dimensioned tape elements may be used. Both distal 60 and proximal ends 62 of the tape element 52 are tapered to facilitate the cuff sizer 50 being inserted and/or passed through tunnels formed in the anal tissues during surgery, and the tape element 52 has a front 64 and back surface 66.

The plurality of holes 54 are aligned in a single row fashion substantially along the longitudinal axis of the tape element 52 and in the embodiment illustrated in FIGS. 2–4, the cuff sizer 50 has eight such holes 54. Corresponding to each hole 54 is an identification mark indicating the circumferences of a body passage such as an anus. For example, the hole 54 marked as "10" refers to a measured circumference of 10 cm. Each of the holes 54 has a diameter of approximately 0.8 cm, and the center to center distance between adjacent holes 54 is 1 cm.

The tape element 52 is flexible such that it can be readily wrapped around a body passage during surgery. In addition, the tape element 52 is compliant to reduce injury to tissue during the surgical procedure. For example, in one embodiment the tape element 52 is formed from a sheet of solid silicone elastomer wherein the sheet is cut into the desired shape, and the plurality of holes are formed during the die cutting process. Other types of flexible polymers such as urethane or other suitable materials known in the art may also be used. Furthermore, the tape element may be formed into the desired shape by other fabrication processes such as machining, injection molding, or other processes known in the art.

Referring to FIGS. 2–4, the adapter 56 is cylindrically shaped and has a distal end 68 and a proximal end 70. The adapter 56 has a length of about 1.5 cm and a diameter of about 0.7 cm, and a flat base portion 72 of the adapter 56 faces the front surface 64 of the tape element 52. The base portion 72 is connected to the top surface 64 of the tape element 52 by a post 74, wherein a receiving slot 76 is formed between the surface of the base portion 72 and the front surface 64 of the tape element 52. The receiving slot 76 is sized such that it is slightly less than the thickness of the tape element 52.

The introducer 58 has a proximal end 78 and a distal end 80 wherein the proximal end 78 is coupled to the distal end 68 of the adapter 56. The introducer 58 may be a flexible tubing with a length of about 32 cm, an outer wall diameter of about 0.3 cm, and an inner wall diameter of about 0.1 cm. A spiral-shaped groove 82 is formed on the surface of the introducer 58 to provide a gripping surface for the surgeon and to enhance longitudinal stretchability. In one preferred embodiment, the adapter 56 and introducer 58 are made of a solid silicone elastomer. However, the adapter and introducer may be formed from various other polymers or suitable materials.

Figure 6:
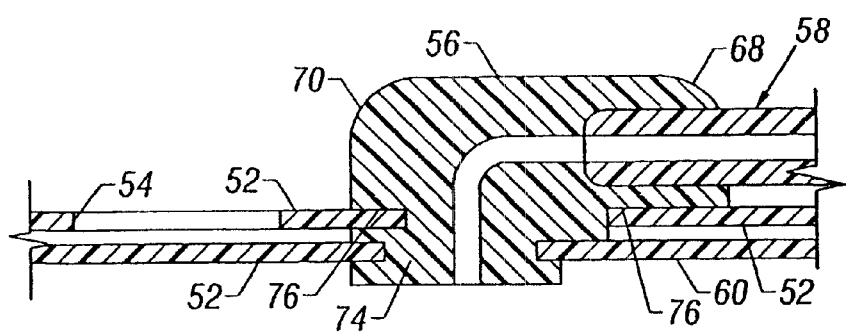
FIG. 6 illustrates a cross-sectional view of the locking cuff sizer along line 5—5 of FIG. 5.
Figure 5:
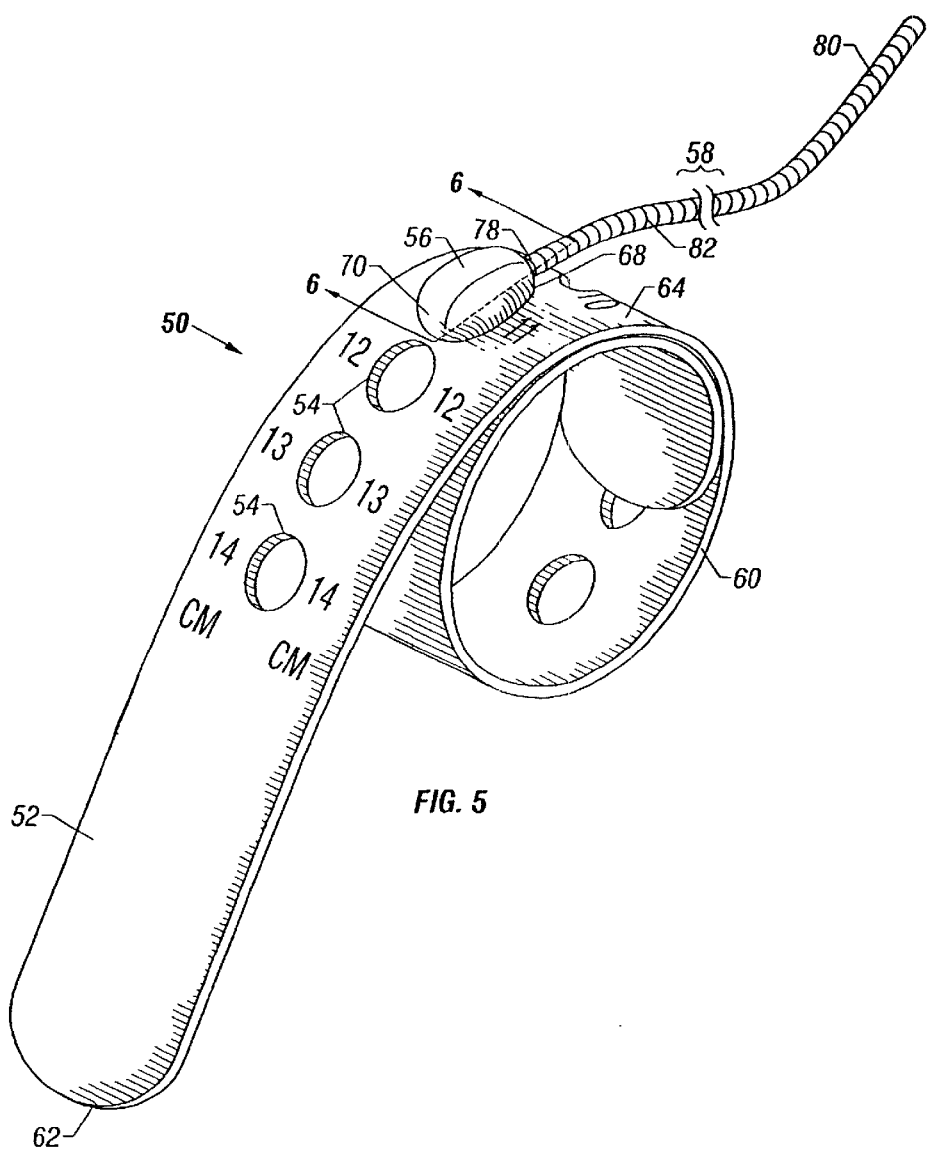
FIG. 5 is a perspective view of the locking cuff sizer of FIG. 2 shown in a "locked" configuration.

Referring to FIGS. 5 and 6, the cuff sizer 50 is shown in its locked position wherein the adapter 56 is lockingly engaged with hole 54 identified by the mark "11". The cuff sizer 50 is manipulated into its "locked" position by passing the introducer 58 from the back surface 66 of the tape element 52 and through the desired hole 54. With the introducer 58 completely drawn through the desired hole 54, the desired hole 54 is stretched as the adapter 56 is passed through the desired hole 54. Thus, the tape element 52 should be adequately resilient to allow the hole 54 to stretch and yet capable of returning to its original, unstressed dimension in order to obtain accurate girth measurements.

Figure 7:
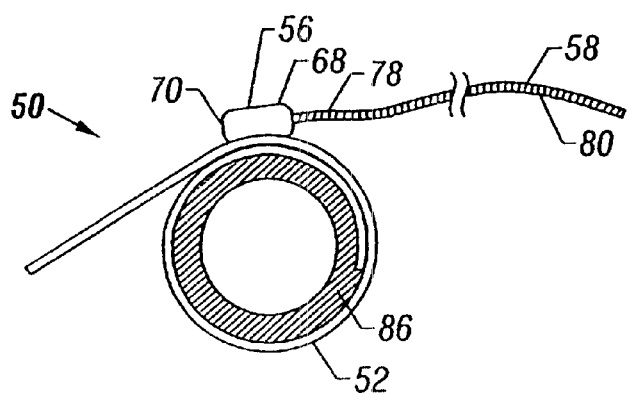
FIG. 7 schematically illustrates the locking cuff sizer shown in FIG. 2 secured to a body passage.

The cuff sizer 50 is in its "locked" position when a side wall 84 of the desired hole 54 is engaged with the receiving slot 76 of the adapter 56. Referring to FIG. 7, the locking cuff sizer 50 is secured around a body passage 86, such as an anus, in order to perform a measurement.

It is noted that the present invention is not limited to the circular hole and adapter configuration described above. Openings such as slits may be used instead of the circular holes, and the adapter may be configured in any form as long as it is able to pass through an opening and "lock" the tape element. In addition, smaller or larger dimensioned cuff sizers may be used. For example, a smaller dimensioned cuff sizer is preferable for determining urethral girth, while larger cuff sizers are preferable for measuring the anus of a large patient. It is contemplated that cuff sizers should be capable of making girth measurements ranging from about 3 cm to about 20 cm, wherein the tape element may have a length of about 10 cm to 35 cm and a width of about 1 cm to 5 cm. Furthermore, the introducer may comprise a wire having non-elastic characteristics or another elongated member such as a cord.

The anal girth of a female patient may be determined according to the following surgical procedure. The patient is placed in a modified lithotomy position on the operating table with legs in Allen stirrups. Two lateral perianal incisions staying extrasphincterically are formed. The incisions are deepened into the ischiorectal fossa. Using blunt finger dissection, a posterior tunnel is formed distal to the coccyx and behind the distal rectum or upper anal canal. Electrocautery may be used to divide tougher tissue. A penrose drain is placed in the posterior tunnel. An anterior tunnel is created extrasphincterically by using blunt finger dissection and using electrocautery to divide tougher tissue. It is noted that other surgical procedures such as a single, anterior-transverse incision may be performed to determine the anal girth.

Once the anterior tunnel is completed, the ideal length of a cuff to be implanted is determined by utilizing the locking cuff sizer. The penrose drain is removed, and the introducer is inserted into a first end of the anterior tunnel. A Statinsky clamp is inserted into a second end of the anterior tunnel and clamped onto the introducer, and the introducer and tape element are drawn through the anterior tunnel. After unclamping the introducer, the introducer is inserted into a first end of the posterior tunnel (the first end of the posterior tunnel is adjacent the second end of the anterior tunnel). The Statinksy clamp is inserted into a second end of the posterior tunnel (the second end of the posterior tunnel is adjacent the first end of the anterior tunnel) and clamped onto the introducer. The introducer and tape element are drawn through the posterior tunnel. At this stage of the surgical procedure, the proximal end of the tape element is extending outside the first end of the anterior tunnel, and the distal end of the tape element is extending outside the second end of the posterior tunnel. As described above, the cuff sizer is manipulated into its "locked" position by passing the distal end of the introducer through the desired hole, and the side wall of the desired hole is engaged with the receiving slot.

Once "locked", the surgeon may evaluate the tightness of the "locked" position by sliding the cuff sizer along the anus. If the cuff sizer is overly tight or loose, it may be "unlocked" and another hole may be selected. When the appropriate hole is selected, measurement of the anus may be noted by viewing the mark which corresponds to the appropriate hole. After determining the correct cuff size, the cuff sizer is removed, and a correctly sized cuff is implanted into the patient. To aid in the implantation of the cuff, the cuff may be attached to the cuff sizer and drawn through the anterior and posterior tunnels as the cuff sizer is removed.

As known to one skilled in the art, a similar surgical procedure may be performed to measure the anal girth of a male patient. Obviously, certain steps may differ due to the anatomical differences between a male and female patient.

Although the present invention has been described in detail with regarding the exemplary embodiment and drawings thereof, it should be apparent to those skilled in the art that various adaptations may be accomplished without departing from the spirit and scope of the invention. Accordingly, the invention is not limited to the precise embodiment shown in the drawings and described in detail hereinabove. For example, the cuff sizer may be "locked" by other means such as snap fasteners comprising a plurality of male sections disposed on a front surface of the tape element and a plurality of female section disposed on the back surface of the tape element, wherein the cuff sizer is "locked" by fastening the male section onto the female section.

What is claimed is:

1. A locking cuff sizer for determining an appropriately sized cuff for a body passage, comprising:
    a tape element having a proximal end and a distal end, said tape element having at least one measuring mark positioned thereon, and said tape element being constructed to be moved through body tissues during a surgical procedure;
    at least one hole disposed on the tape element, said at least one hole formed corresponding to said at least one measuring mark; and
    an adapter disposed at the distal end of the tape element;
    whereby the adapter is engageable with one of said at least one hole to substantially lock the locking cuff sizer.

2. The locking cuff sizer of claim 1, further comprising an elongated element having a proximal end and a distal end, the proximal end of the elongated element being connected to the adapter.

3. The locking cuff sizer of claim 2, wherein the elongated element is a flexible tubing.

4. The locking cuff sizer of claim 2, wherein said elongated element comprises a gripping surface.

5. The locking cuff sizer of claim 4, wherein said gripping surface comprises a spiral-shaped groove.

6. The locking cuff sizer of claim 2, wherein said elongated element has a length of about 32 cm.

7. The locking cuff sizer of claim 1, wherein a diameter of the at least one hole is less than the length of the adapter, and wherein one of the at least one hole is capable of being stretched to accept the adapter.

8. The locking cuff sizer of claim 1, having a plurality of holes, the plurality of holes substantially aligned in a single row and positioned to correspond to a circumference measurement ranging from approximately 3 cm to approximately 20 cm.

9. The locking cuff sizer of claim 1, having a plurality of holes, wherein a center of each of the holes is spaced 1 cm from an adjacent center of the hole.

10. The locking cuff sizer of claim 1, wherein the tape element has a maximum length of about 35 cm.

11. The locking cuff sizer of claim 1, wherein the tape element has a width ranging from about 1 cm to about 5 cm.

12. The locking cuff sizer of claim 1, wherein the at least one measuring mark comprises at least two measuring marks that correspond to two different sizes of cuffs for an artificial bowel sphincter.

13. The locking cuff sizer of claim 12, wherein the body passage is an anus.

14. A method for estimating the girth of a body passage, comprising:
    (a) providing a locking cuff sizer comprising:
        a flexible tape element having a proximal end and a distal end, said tape element having at least one measuring mark formed thereon;
        a plurality of holes disposed on the tape element; and
        an adapter disposed towards the distal end of the tape element;
    (b) placing the flexible tape element substantially around a circumference of the body passage; and
    (c) securing the tape element around the circumference of the body passage by engaging the adapter with one of the plurality of holes.

15. The method of claim 14, further comprising evaluating the tightness of the locked position by sliding the locking cuff sizer along the body passage.

16. The method of claim 14, wherein the locking cuff sizer is used for determining a correctly sized cuff for an artificial bowel sphincter.

17. The method of claim 16, wherein the body passage is an anus.

18. The method of claim 14, wherein the locking cuff sizer is used for determining a correctly sized cuff for an artificial urinary sphincter.

19. The method of claim 18, wherein the body passage is a urethra.

20. The method of claim 14, further comprising attaching a flexible tube to the adapter.

21. The method of claim 20 wherein step (c) further comprises passing the flexible tube through one of the plurality of holes.

22. The method of claim herein the tape element has a first surface and a second surface, the adapter extends outwardly from the first surface of the tape element, and wherein the second surface of the tape element contacts a surface of the body passage.

23. The method of claim 14 further comprising:
    providing an introducer having a gripping surface disposed thereon; and
    attaching said introducer to said adapter.

24. The method of claim 23, wherein step (c) further comprises passing said introducer through one of the plurality of holes.

25. The method of claim 24, wherein the flexible tape element has a first surface and a second surface, the adapter extends outwardly from the first surface of the tape element, and wherein the second surface of the tape element contacts a surface of the body passage.

26. An apparatus for measuring the size of a body passage comprising:
    a flexible strip having first and second ends and being substantially uniform in width along the length of said flexible strip;
    at least one aperture disposed on the strip between the first and second ends;
    said strip being constructed to be moved through body tissues during a surgical procedure;
    an indicia of body passage diameter disposed on the strip in association with the at least one aperture; and
    an elongated element having first and second ends, the elongated element being sized and shaped to draw the flexible strip through body tissue.

27. The apparatus of claim 26, further comprising an adapter disposed at the first end of the flexible strip, wherein the adapter engages with the at least one aperture to lock the apparatus.

28. The apparatus of claim 26, wherein the elongated element is a flexible tubing.

29. The apparatus of claim 26, wherein the body passage is an anus, and the apparatus is a cuff sizer for determining a correctly sized cuff for an artificial bowel sphincter.

30. The apparatus of claim 26, wherein the body passage is a urethra, and the apparatus is a cuff sizer for determining a correctly sized cuff for an artificial urethral sphincter.

31. The apparatus of claim 26 wherein said elongated element comprises a gripping surface.

32. The apparatus of claim 31 wherein said gripping surface comprises a spiral-shaped groove.

33. A method for measuring the size of a body passage comprising:
(a) providing a flexible strip of material having an indicia of body passage diameter located on the flexible strip;
(b) inserting the flexible strip into a dissected tunnel around the body passage;
(c) manipulating the strip such that the strip substantially surrounds the body passage; and
(d) observing the indicia on the strip to generally determine the body passage diameter.

34. The method of claim 33, wherein step (a) further comprises providing a plurality of holes aligned along a longitudinal axis of the strip, and providing an adapter disposed at a first end of the strip and step (c) further comprises locking the strip around the circumference of the body passage by securing the adapter onto one of the plurality of holes.

35. The method of claim 34, further comprising evaluating the tightness of the locked strip by sliding the strip along the body passage.

36. The method of claim 33, wherein the strip is used for determining a correctly sized cuff for an artificial bowel sphincter.

37. The method of claim 33, wherein the body passage is an anus.

38. The method of claim 33, wherein the strip is used for determining a correctly sized cuff for an artificial urinary sphincter.

39. The method of claim 33, wherein the body passage is a urethra.

40. The method of claim 33, further comprising attaching a cuff to the strip and implanting the cuff by withdrawing the strip from the dissected tunnel.

* * * * *